(12) United States Patent
Portnoy

(10) Patent No.: US 7,032,598 B2
(45) Date of Patent: Apr. 25, 2006

(54) SNOREWAY SPACE BLOCK WITH SNORE STRIPS OR PORTNOY BUCCAL TAB

(76) Inventor: Leonard L. Portnoy, 2112 Century Park La., #118, Los Angeles, CA (US) 90067

(*) Notice: Subject to any disclaimer, the term of this patent is extended or adjusted under 35 U.S.C. 154(b) by 0 days.

(21) Appl. No.: 10/290,828

(22) Filed: Nov. 8, 2002

(65) Prior Publication Data

US 2004/0089310 A1    May 13, 2004

(51) Int. Cl.
*A61F 5/56* (2006.01)

(52) U.S. Cl. ............... 128/848; 602/902; 128/859

(58) Field of Classification Search ............... 128/846, 128/848, 859–862; 602/902
See application file for complete search history.

(56) References Cited

U.S. PATENT DOCUMENTS

| 1,216,679 | A | * | 2/1917 | Foster | 128/848 |
| 1,354,652 | A | * | 10/1920 | Jeffries | 128/848 |
| 2,574,623 | A | | 11/1951 | Clyde | |
| 4,711,237 | A | | 12/1987 | Kaiser | |
| 4,817,636 | A | * | 4/1989 | Woods | 128/848 |
| 4,883,072 | A | | 11/1989 | Bessler | |
| 5,640,974 | A | | 6/1997 | Miller | |
| 5,690,121 | A | | 11/1997 | Miller | |
| 6,089,232 | A | | 7/2000 | Portnoy et al. | |

FOREIGN PATENT DOCUMENTS

| DE | 38 37 277 A1 | * | 5/1990 |
| FR | 2 574 657 | * | 12/1984 |
| WO | WO 9013277 | * | 4/1990 |
| WO | 32350 A1 | * | 4/2002 |

* cited by examiner

*Primary Examiner*—Michael A. Brown
(74) *Attorney, Agent, or Firm*—Lewis Brisbois Bisgaard & Smith LLP; Sanford Astor

(57) ABSTRACT

A method and device for stopping a person from snoring while sleeping comprising a narrow strip having adhesive covering one surface or a buccal tab which can be affixed to a snore prevention intra-oral device, both of which block the snoreway space of the person.

5 Claims, 2 Drawing Sheets

SNOREWAY SPACE BLOCK WITH SNORE STRIPS OR PORTNOY BUCCAL TAB

This invention is described in my Disclosure Documents #520275 filed Oct. 21, 2002 and #520183 filed Oct. 22, 2002.

BACKGROUND OF THE INVENTION

It has been estimated that ninety million American adults and children snore and that one in every ten adults snores. Although snoring has no serious medical consequences for most people, for an estimated one in one hundred snorers, habitual snoring is the first indication of a potentially life-threatening sleep disorder called Obstructive Sleep Apnea. If not diagnosed or if left untreated, Obstructive Sleep Apnea could result in severe medical consequences such as systemic high blood pressure, cardiovascular disease and even sudden death.

Many people think that snoring and apnea are the same thing. This is not true. Snoring, which is caused by vibration of the tissues due to air turbulence as the airway narrows, may be a sign that a patient is suffering from apnea. But not all snorers suffer from apnea.

Snoring can be categorized by its severity. At one end of the scale is the benign snorer who snores but experiences no physical problems. On the other end is the snorer who suffers from apnea, and in the middle is the snorer who suffers from upper airway resistance syndrome. In these people, though they may not actually experience apneic episodes, their snoring is so loud and their breathing so labored, that it still wakes them, and their partners, numerous times throughout the night.

Millions of spouses, partners and/or children suffer through the night by the annoying noise of the snorer. Snoring not only disturbs the sleeping pattern of the snorer himself, it is also disruptive to the family life by causing lack of sleep to all involved. This leaves all involved unrefreshed, tired and sleepy throughout the day. It can cause sleepiness while driving, reading, working or doing other tasks.

Snoring generally comes from opening the mouth while sleeping. A broad variety of intra-oral and dental appliances and devices are now available to treat a patient for snoring. The known oral devices for treating snoring and obstructive sleep are worn inside of the mouth and work by repositioning of the jaw, moving the mandible, lifting the soft palate or moving the tongue forward. The various classes of treatment devices that now exist include mandibular advancers and tongue advancers. These appliances work by advancing the tongue and jaw away from the back wall of the throat. The tongue advancers are used when the jaw joints do not tolerate stretching or when there are insufficient teeth to support a mandibular advancer. Other methods used to treat snoring include controlled positive air flow pressure systems also known as CPAP which require a nose mask and which are quite uncomfortable. The function of the CPAP treatment is enhanced using Applicant's invention.

All of these known devices suffer from having to be worn inside of the mouth, they are uncomfortable to wear and they are expensive and must be fitted and made to order. These devices also often cause excessive salivation, dry mouth or tempomandibular joint (TMJ) discomfort.

Other treatments for snoring include various surgeries, which are drastic steps to take to attempt to cure the problem, however snoring can be so disruptive to a person's life and relationships, that some sufferers resort to surgery.

Another device which has been known is that described in U.S. Pat. Nos. 5,640,974 and 5,690,121 to Miller. Miller's device comprises a flexible sheet with adhesive, cut in a U-shape. It attempts to keep the mouth closed by covering only the "remote end" of the lips. It is highly ineffective because the two "cheek attachment" strips come loose very easily with any movement of the mouth and the entire device falls off, and because the limited covering of the mouth and lips is ineffective to keep the mouth closed. In addition, the loose ends make it difficult to apply and the backing of the tape difficult to peel off.

My prior patent. U.S. Pat. No. 6,089,232, describes a method of using tape to keep the mouth closed which aids in preventing snoring. Further research however has shown that blockage of the "snoreway space" as described herein, is both easier to use and more effective in preventing snoring.

OBJECTS OF THE INVENTION

Accordingly, several objects and advantages of the invention are as follows:

It is an object of this invention to provide a simple treatment to prevent snoring.

It is another object of this invention to provide a device, easily applied and easily tolerated, which will substantially prevent snoring.

Yet a further object of the invention is to provide an addition to existing intra oral devices, which makes the devices substantially better at preventing snoring.

Further objects and advantages will become apparent from a consideration of the following description and drawings.

DETAILED DESCRIPTION OF THE INVENTION

Figure 1:
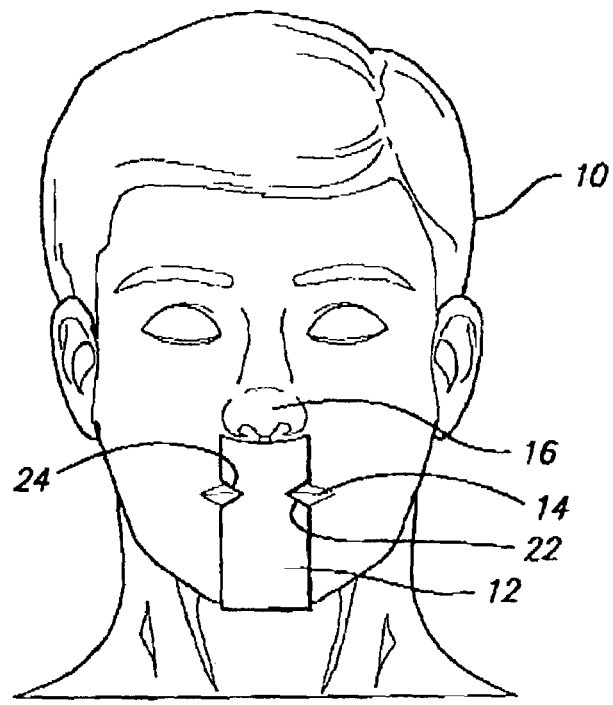
FIG. 1 is a front view of a person wearing the snoreway space block of this invention.
Figure 2:
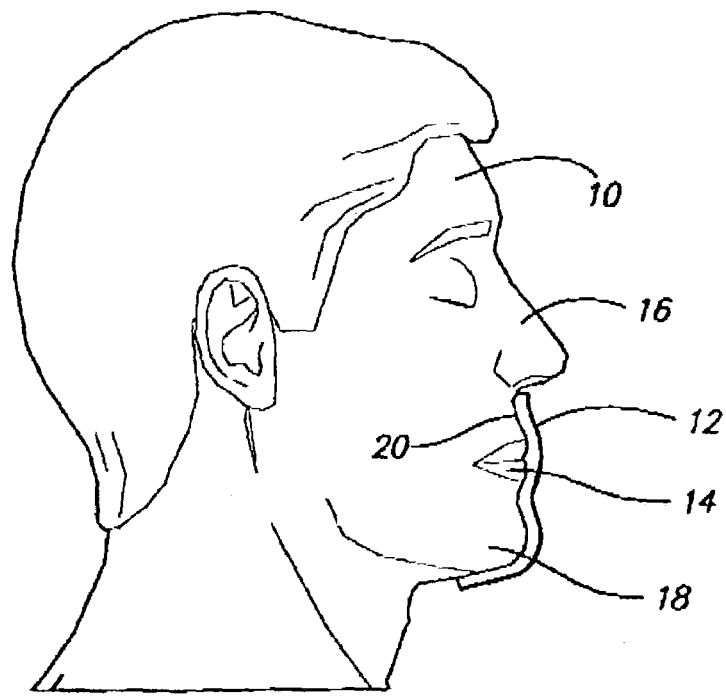
FIG. 2 is a side view of a person wearing the device.

Referring now to FIGS. 1 and 2, there is shown a person 10 having a narrow adhesive strip 12 covering the center of the person's mouth 14. FIG. 2 shows that adhesive strip 12 may run from below the nose 16, or sides of nose 16, down under the chin 18. This is to provide security that adhesive strip 12 will stay attached during the night and keep the mouth from opening.

The adhesive strips 12 may come packaged as a roll of tape or the strips may be packaged one or more in a sterile container, such as a paper cover similar to band-aids. One side of the strip 12 has an adhesive to attach to the face, as shown, and the other side is non-adhesive. If packaged as individual strips, there would be a peel-off, protective cover (not shown) which covers the adhesive side 20 of strip 12 until used.

Indentations or cut-outs 22 and 24 are provided to provide an airway to the mouth so that breathing through the mouth may occur. But, because the snoreway space is covered, the strip 12 is very effective in significantly reducing snoring.

Strip 12 can be made from any fabric or material having an adhesive backing, such as "Hypafix" manufactured by, and a trademark of, Smith & Nephew, and sold as a dressing retention sheet. A similar product is manufactured by Beirsdorf, Inc. under the trademark "Cover-Roll" stretch. Both of these materials are cross-elastic, that is, elastic in all directions, which greatly aids in the effectiveness of the snoreway space block of this invention. These products are also hypo-allergenic and self-adhesive.

The snoreway space is defined as approximately the center third of the width of the lips. The exact width of the strips 12 will vary, depending upon the size of a person's lips.

The strips will vary from about ½" to about 2" wide, and from about 4" to about 5" long. Strip 12 is applied to the face of the user, usually just before going to bed for the night.

Figure 4:
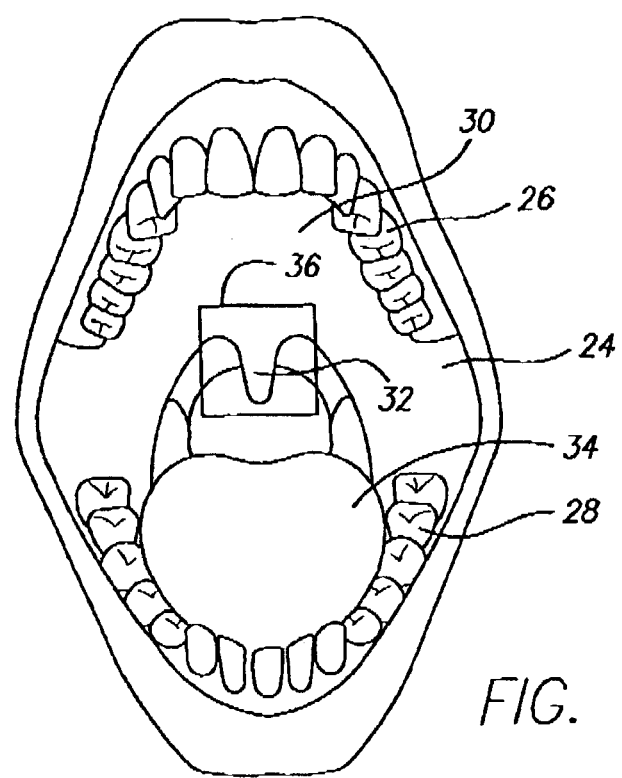
FIG. 4 is a depiction of the snoreway space.

FIG. 4 depicts the open mouth 24 with the upper and lower teeth 26 and 28. There is shown the soft palate 30 and the uvula 32. The tongue 34 lies below the level of the teeth. A rectangle 36 has been drawn in to show the location of the snoreway space.

Figure 3:
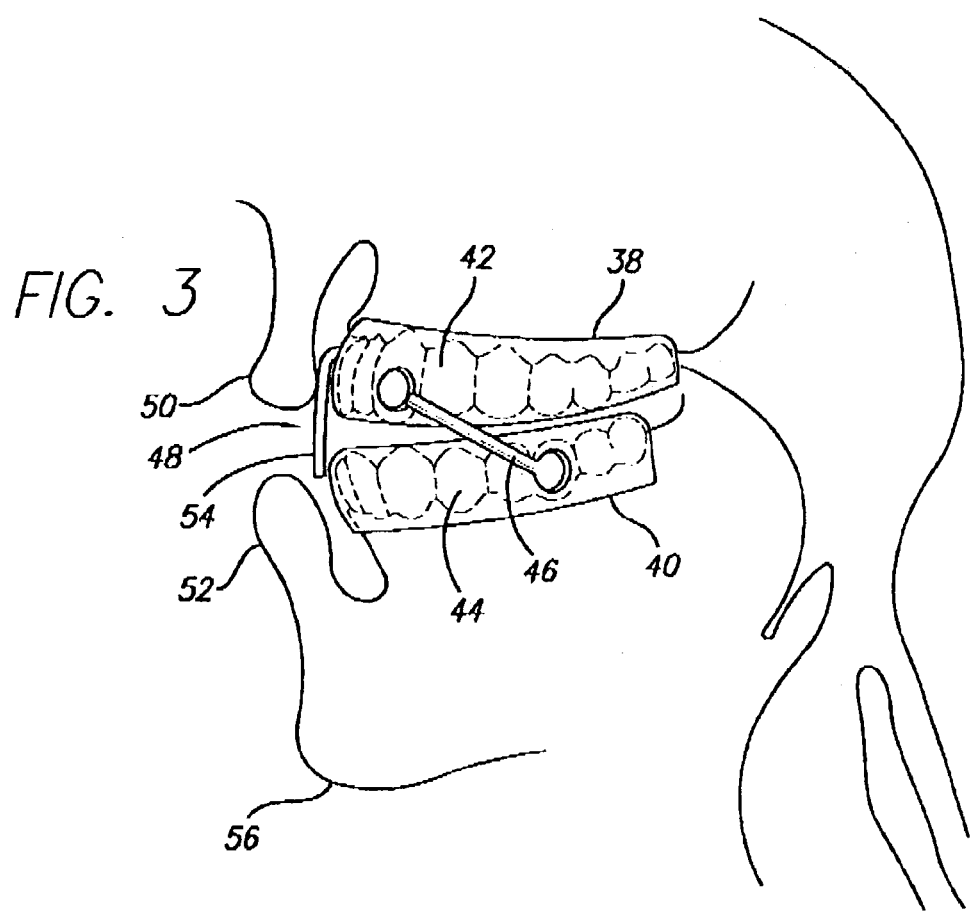
FIG. 3 is a side view of another embodiment of the device.

Referring to FIG. 3, there is shown another embodiment of the invention. As described in the background of the invention above, there are many, many intra-oral dental devices which are now used to try to prevent snoring. One of these is depicted in FIG. 3. The device operates by providing an upper appliance 38 and a lower appliance 40 which cover the upper teeth 42 and the lower teeth 44 respectively. A brace 46, and a corresponding brace on the opposite side of the mouth (not seen) hold the mouth 48 in a slightly open position but do not allow the jaw 56 to open any further than the distance fixed by the brace 46. This alone has been proven to reduce snoring.

However the addition of a "buccal tab" 54 which is attached to the upper appliance across the center of the mouth 48 greatly reduces snoring even further. The Buccal tab 54 is a small rectangular tab which covers the snoreway space as defined above and is essentially the size of the rectangle 36 shown in FIG. 4. It blocks off the uvula and part of the soft palate. The buccal tab may be attached to any known intra-oral device that is now used to alleviate snoring so long as the device has a front portion to which the tab may be attached. This blocks off about the middle one-third of the air space created by the lips. Because most of the noise of snoring comes from the area of the uvula, the 22 buccal tab minimizes the vibrations and sound which normally comes from the snorer. The snorer can, in the alternative, wear the adhesive strip 12.

With either the strips 12 or the buccal tab 54, the user can both breath and talk, but cannot open his or her mouth more than a very small opening, which allows breathing but effectively prevents snoring.

Both the strip 12 and the buccal tab 54 have proven quite effective in substantially preventing snoring by blocking the snoreway space. This invention has been tested on individuals with snoring problems and it has prevented snoring while sleeping. Furthermore, the persons tested have experienced little or no discomfort. The device of this invention is the easiest, least expensive, yet most effective treatment for severe snoring problems yet devised.

Having thus described the invention, it is requested that the invention be described by the scope of the following claims.

I claim:

1. A method for preventing a person from snoring while sleeping comprising affixing a narrow strip having an adhesive backing, extending from under the person's chin or from the sides of the nose to under the person's chin, over the center of the mouth and upper and lower lips of the person, tightly enough to prevent the person's mouth from opening during sleep any more than a very small opening but loosely enough to allow the person to both breath and talk through the mouth.

2. The method of claim 1 in which the narrow strip covers the snoreway space of the person.

3. The method of claim 1 in which the strip is affixed so as to cover about to center one-third of the lips.

4. The method of claim 1 further comprising cutting a pair of indentations in the strip, adjacent the outer edges of the lips.

5. The method of claim 1 in which the narrow strip is from about one-half inch to about 2 inches wide and from about 2 inches to about 5 inches long.

* * * * *